US00RE36331E

United States Patent [19]

Arduini

[11] E Patent Number: Re. 36,331

[45] Reissued Date of Patent: Oct. 5, 1999

[54] USE OF L-CARNITINE AND ALKANOYL L-CARNITINES IN THE STORAGE OF BLOOD FOR TRANSFUSIONS AND STABILIZING SOLUTIONS CONTAINING THEM

[75] Inventor: Arduino Arduini, Pescara, Italy

[73] Assignee: Sigma-Tau Industrie Farmaceutiche Riunite S.p.A., Rome, Italy

[21] Appl. No.: 09/035,028

[22] Filed: Mar. 5, 1998

Related U.S. Patent Documents

Reissue of:

[64] Patent No.: 5,496,821
Issued: Mar. 5, 1996
Appl. No.: 08/253,275
Filed: Jun. 2, 1994

[30] Foreign Application Priority Data

Jun. 2, 1993 [IT] Italy ..... RM93A0364

[51] Int. Cl.[6] ..... A61M 31/35; A61M 31/535; A61M 5/00; A01N 43/16

[52] U.S. Cl. ..... 514/228.8; 514/451; 514/459; 514/460; 514/937; 604/4; 604/7; 604/403; 604/416

[58] Field of Search ..... 514/228.18, 451, 514/459, 460, 937; 604/4, 7, 403, 416

[56] References Cited

U.S. PATENT DOCUMENTS

| | | | |
|---|---|---|---|
| 4,434,160 | 2/1984 | Jeretin et al. | 424/180 |
| 4,731,360 | 3/1988 | Alexander et al. | 514/201 |
| 4,839,159 | 6/1989 | Winter et al. | 424/59 |
| 4,968,714 | 11/1990 | Brevetti | 514/556 |

*Primary Examiner*—Nathan M. Nutter
*Attorney, Agent, or Firm*—Oblon, Spivak, McClelland, Maier & Neustadt, P.C.

[57] ABSTRACT

Solutions which contain L-carnitine and alkanoyl L-carnitine are useful for stabilizing blood for transfusions.

15 Claims, 2 Drawing Sheets

USE OF L-CARNITINE AND ALKANOYL L-CARNITINES IN THE STORAGE OF BLOOD FOR TRANSFUSIONS AND STABILIZING SOLUTIONS CONTAINING THEM

Matter enclosed in heavy brackets [ ] appears in the original patent but forms no part of this reissue specification; matter printed in italics indicates the additions made by reissue.

*CONTINUING APPLICATION DATA*

*This application is a Reissue application of Ser. No. 08/253,275, filed Jun. 2, 1994, U.S. Pat. No. 5,496,821.*

BACKGROUND OF THE INVENTION

FIELD OF THE INVENTION

The present invention consists in a new non-therapeutic use of L-carnitine, alkanoyl L-carnitines and their pharmacologically acceptable salts as preservative agents for blood transfusions.

The present invention also consists in new stabilizing solutions for the storage of blood containing L-carnitine, alkanoyl L-carnitines or their pharmacologically acceptable salts.

What is meant by alkanoyl L-carnitines are acetyl, propionyl, butyryl, isobutyryl, valeryl and isovaleryl L-carnitine. Hereinafter, for reasons of simplicity, we shall refer only to L-carnitine, in the understanding, however, that the description also applies to the above-mentioned alkanoyl L-carnitines and their pharmacologically acceptable salts.

As is well known, L-carnitine is necessary for the translocation of fatty acids within the mitichondria where betaoxidation takes place.

Various uses of L-carnitine are known, but all of these are of a therapeutic nature. For instance, L-carnitine is used in the cardiovascular field for the treatment of acute and chronic myocardial ischaemia, angina pectoris, heart failure and cardiac arrhythmias.

In the nephrological field, L-carnitine is administered to chronic uraemics undergoing regular haemodialytic treatment to combat myasthenia and the onset of muscular cramps.

Other therapeutic uses have to do with the normalization of the HDL:LDL+VLDL ratio and total parenteral nutrition. There is, however, no relationship between the known therapeutic uses of L-carnitine mentioned previously and the use envisaged in the present invention.

It is well known that the essential factors for good storage of blood in the liquid state are the temperature and the composition of the stabilizing solution.

The temperature must be such as to allow a reduction of the metabolic activity of the erythrocytes without damaging them. The optimal temperature is 4° C.±2° C.

The stabilizing solutions must be able to make the blood unclottable, to reduce the glycolytic activity of the red blood cells and, at the same time, permit such activity by providing an adequate substrate.

The efficacy of a stabilizing solution is assessed by observing both the alterations arising in the erythrocytes in vitro and their survival in vivo, after variable periods of storage at optimal temperature.

The alterations to the erythrocytes in vitro can be checked by evaluating the amount of haemoglobin released by the erythrocytes, their osomotic and mechanical fragility, the changes in their shape and volume and the chemical changes they undergo.

The stabilizing solutions used to date do not allow good storage of blood for more than 14 to 21 days.

For instance, if the blood is collected in ACD (citric acid-sodium citrate-dextrose), one of the most widely used stabilizing solutions in the past, and transfused after 14 or 21 days of storage, the in-vivo survival rates of erythrocytes 24 h after transfusion are 90 and 80%, respectively; it is also well known that the red blood cells that remain in circulation 24 h after transfusion have a survival rate equal to that of fresh blood.

During storage, erythrocytes undergo alterations with formation of spherocytes and burr cells. The erythrocytes swell and lose potassium and haemoglobin, which then increases in the plasma. At the same time there is a reduction in 2,3-DPG (2,3-diphosphoglycerate) and thus an increase in the affinity of haemoglobin for oxygen, which is released to tissues in smaller amounts.

The alterations of erythrocytes stored in ACD may be at least partly corrected by adding phosphate to the stabilizing solution. Thus CPD (citrate-phsophate-dextrose) solutions have come to be used for the storage of blood and are now the ones most commonly employed The addition of phosphate gives rise to the maintenance of a higher level of 2,3-DPG and thus a lower affinity of haemoglobin for oxygen. However, the in-vivo survival of erythrocytes stored in CPD is little better, if not indeed identical to that of erythrocytes stored in ACD.

SUMMARY OF THE INVENTION

It has now been found that the addition of L-carnitine or of one of its pharmacologically acceptable salts to the usual stabilizing solutions for the storage of blood for transfusions has the effect of dramatically improving in-vitro survival of erthrocytes and of reducing the formation of spherocytes and burr cells and the loss of haemoglobin in the plasma. As a result of these beneficial effects, the period of good storage of blood for transfusion purposes is more than doubled compared to traditional solutions.

Thus, the invention described herein consists in the use of L-carnitine and its pharmacologically acceptable salts for the production of stabilizing solutions for the storage of blood for transfusions.

DETAILED DESCRIPTION OF THE PREFERRED EMBODIMENTS

Viewed from a different angle, the invention also consists in stabilizing solutions for the storage of blood for transfusion characterized by the fact that they contain L-carnitine or one of its pharmacologically acceptable salts.

What is meant by pharmacologically acceptable salts of L-carnitine, apart from the L-carnitine internal salt, is any L-carnitine salt with an acid which does not give rise to unwanted side effects. These acids are well known to pharmacologists and to experts in pharmacy.

Non-exclusive examples of such salts are chloride, bromide, orotate, aspartic acid, acid citrate, acid phosphate, fumarate and acid fumarate, maleate and acid maleate, acid oxalate, acid sulphate, glucose phosphate, tartrate and acid tartrate.

These solutions are characterized by the fact that they contain 0.5–10.0 mM/L, and preferably 4–6 mML of L-carnitine or an equivalent amount of one of its pharmacologically acceptable salts.

An example of a stabilizing solution according to the invention is composed of:

| | |
|---|---|
| Glucose | 80–120 mM/L |
| Mannitol | 40–60 mM/L |
| $K_2HPO_4$ | 24–28 mM/L |
| $KH_2PO_4$ | 12–16 mM/L |
| Potassium citrate | 15–20 mM/L |
| L-carnitine, internal salt | 4–6 mM/L |

BRIEF DESCRIPTION OF THE DRAWINGS

The efficacy of L-carnitine in the use envisaged in this invention is verified by numerous studies, one of which is reported here below with reference to the attached diagrams, where.

EXAMPLES

Figure 1:
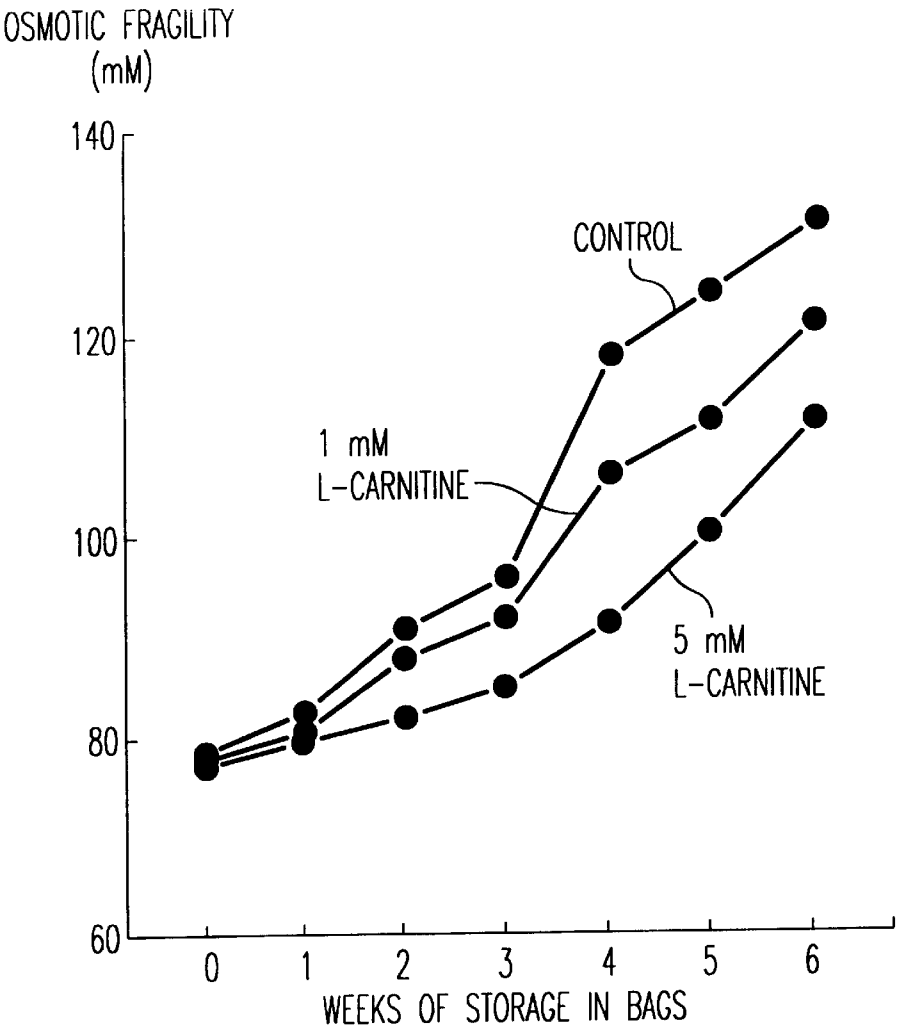
FIG. 1 is a graph representing the osomotic fragility of eythrocytes as a function of storage time (expressed in weeks)
Figure 2:
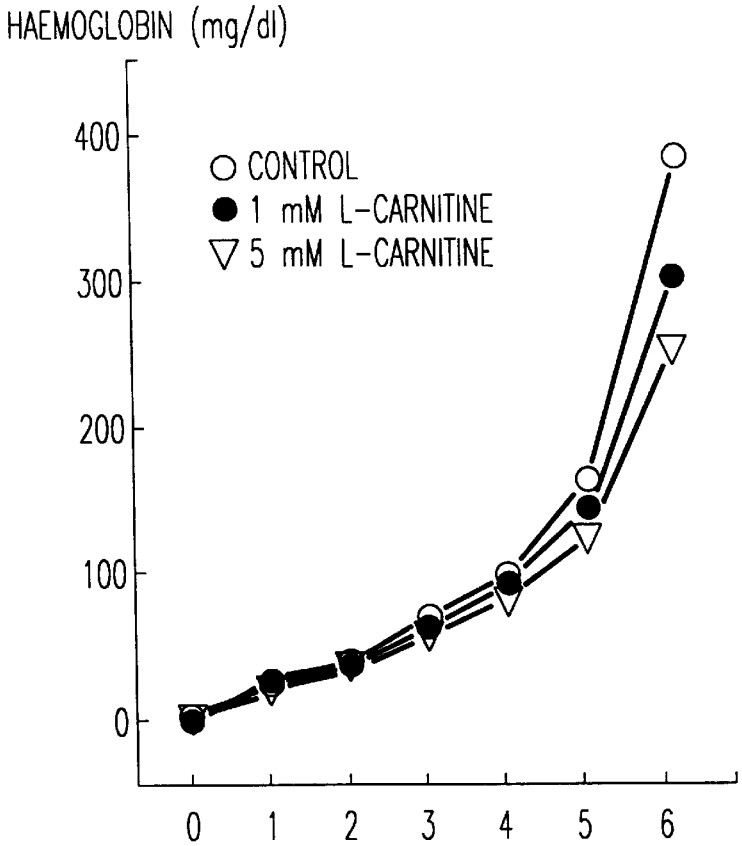
FIG. 2 is a graph representing the haemoglobin concentration (in mg/dL) in the storage medium as a function of storage time (expressed in weeks)
Figure 3:
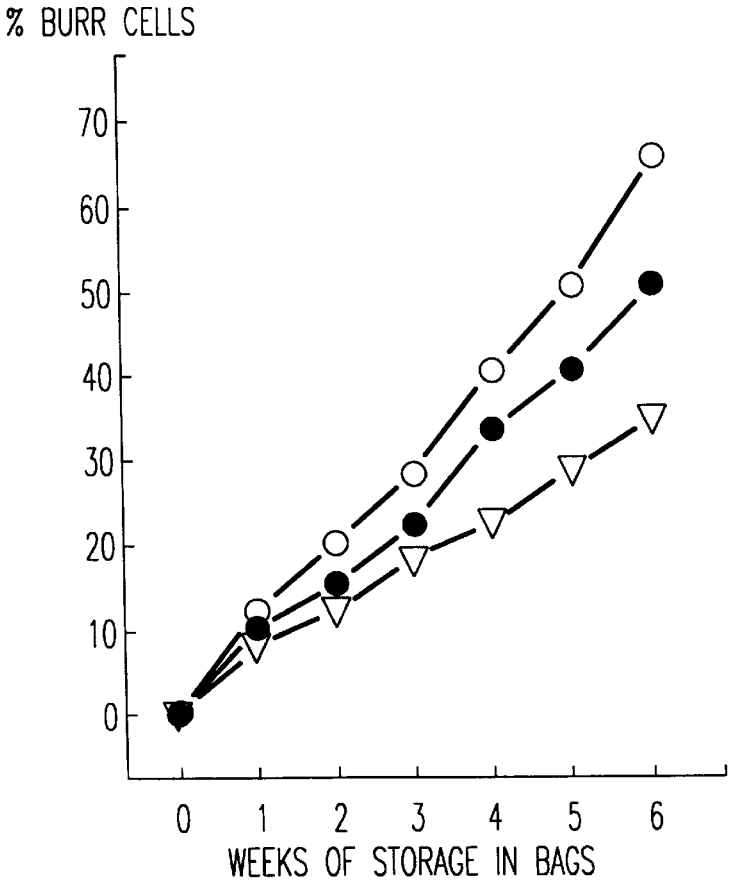
FIG. 3 is a graph representing the percentage of burr cells in the storage medium as a function of storage time (expressed in weeks).

Admitted to this study were volunteers who were habitual blood donors and who were perfectly healthy at the time the blood samples were taken. The blood samples were collected in special quadruple bags normally used for blood storage Baxter, Fenwal Division, La Chatre, France) containing CPDA-1 (CPDA-1 composition: 110 mM glucose; 55 mM mannitol; 25.8 mM $K_2HPO_4$; 14.7 mM $KH_2PO_4$; 17.9 mM potassium citrate), an iso-osmolar fluid commonly used for the storage of blood at 5° C. The blood was poured into the above-mentioned bags by means of a centrifuge which allowed the formed elements of the haematic mass to be separated from the erythrocytes. In addition to the above-mentioned CPDA-1, some of the bags contained L-carnitine, which was always introduced under conditions of maximum sterility. The ratio of the volume of the storage fluid to the volume of the erythrocytes was close to 1:1. The bags were then placed in refrigerators at a constant temperature of 5° C.

In the course of storage, aliquots of erythrocytes were collected at weekly intervals for the purpose of conducting a number of microscopic and biochemical examinations. The eryrocyte suspension was immediately examined under a phase-contrast microscope to estimate the percentage content of burr cells, which are pathological erythrocytes with a star-type morphology. Later, the eryrthocyte suspension was centrifuged, and the buffy coat was used to determine the haemoglobin content according to a method involving the derivatization of the latter to cyanomethaemoglobin (International Committee for Standardization in Haematology, S. Clin. Pathol. (1978), 31:139–145). The haemoglobin content measured is an indicator of the degree of haemolysis the erythrocyte undergoes in the course of storage in the bags. Lastly, erythrocyte osmotic fragility was evaluated according to the method of Dacie and Lewis (Dacie J. V. and Lewis S. M., Practical Haematology, New York: Churchill Livingstone, 1984: 152–6). The osmotic fragility was calculated as the amount of sodium chloride necessary (in mM/L) to obtain 50% haemolysis.

I claim:

1. A method for stabilizing blood for transfusion, comprising mixing blood with a solution, said solution comprising L-carnitine, alkanoyl L-carnitine, or a pharmaceutically acceptable salt thereof, wherein said pharmaceutically acceptable salt is selected from the group consisting of chloride, bromide, orotate, aspartic acid, acid citrate, acid phosphate, fumarate, acid fumarate, maleate, acid maleate, acid oxalate, acid sulfate, glucoses phosphate, tartrate, and acid tartrate, and wherein said solution comprises 0.5–10.0 mM/L of said L-carnitine, said alkanoyl L-carnitine, or said pharmaceutically acceptable salt thereof.

2. The method of claim 1, wherein said alkanoyl L-carnitine is selected from the group consisting of acetyl L-carnitine, propionyl L-carnitine, butyryl L-carnitine, isobutyryl L-carnitine, valeryl L-carnitine, and isovaleryl L-carnitine.

3. The method of claim 1, wherein said solution comprises:

| | |
|---|---|
| Glucose | 80–120 mM/L |
| Mannitol | 40–60 mM/L |
| $K_2HPO_4$ | 24–28 mM/L |
| $KH_2PO_4$ | 12–16 mM/L |
| Potassium citrate | 15–20 mM/L |
| L-carnitine, internal salt | 4–6 mM/L. |

4. The method of claim 1, wherein said solution comprises 4–6 mM/L of said L-carnitine, said alkanoyl L-carnitine, or said pharmaceutically acceptable salt.

5. The method of claim 1, wherein said solution is mixed with said blood in a ratio to obtain a ratio of volume of solution to volume of erythrocytes of about 1:1.

6. A transfusion bag which comprises:

(a) a sample of whole blood;

(b) a preservative-anticoagulant solution; and (c) 4–6 mM/L of L-carnitine, alkanoyl L-carnitine or a pharmaceutically acceptable salt thereof, wherein said pharmaceutically acceptable salt is selected from the group consisting of chloride, bromide, orotate, aspartic acid, acid citrate, acid phosphate, fumarate, acid fumarate, maleate, acid maleate, acid oxalate, acid sulfate, glucoses phosphate, tartrate, and acid tartrate.

7. The transfusion bag of claim 6, wherein said preservative-anticoagulant solution is selected from ACD, CPD and CPDA-1.

8. The transfusion bag of claim 6, wherein said alkanoyl L-carnitine is selected from the group consisting of acetyl L-carnitine, propionyl L-carnitine, butyryl L-carnitine, isobutyryl L-carnitine, valeryl L-carnitine, and isovaleryl L-carnitine.

*9. A method for stabilizing a composition for transfusion comprising erythrocytes, said method comprising mixing said composition with a solution, said solution comprising L-carnitine, alkanoyl L-carnitine, or a pharmaceutically acceptable salt thereof, wherein said pharmaceutically acceptable salt is selected from the group consisting of chloride, bromide, orotate, aspartic acid, acid citrate, acid phosphate, fumarate, acid fumarate, maleate, acid maleate, acid oxalate, acid sulfate, glucose phosphate, tartrate and acid tartrate, and wherein said solution comprises 0.5–10.0 mM/L of said L-carnitine, said alkanoyl L-carnitine, or said pharmaceutically acceptable salt thereof.*

*10. A transfusion bag which comprises:*

*(a) a composition comprising erythrocytes;*

*(b) a preservative-anticoagulant solution; and*

*(c) 4–6 mM/L of L-carnitine, alkanoyl L-carnitine or pharmaceutically acceptable salt thereof, wherein said*

*pharmaceutically acceptable salt is selected from the group consisting of chloride, bromide, orotate, aspartic acid, acid citrate, acid phosphate, fumarate, acid fumarate, maleate, acid maleate, acid oxalate, acid sulfate, glucose phosphate, tartrate and acid tartrate, and wherein said solution comprises 0.5–10.0 mM/L of said L-carnitine, said alkanoyl L-carnitine, or said pharmaceutically acceptable salt thereof.*

*11. The method of claim 9, wherein said alkanoyl L-carnitine is selected from the group consisting of acetyl L-carnitine, propionyl L-carnitine, butyryl L-carnitine, isobutyryl L-carnitine, valeryl L-carnitine, and isovaleryl L-carnitine.*

*12. The method of claim 9, wherein said solution comprises:*

| | |
|---|---|
| Glucose | 80–120 mM/L |
| Mannitol | 40–60 mM/L |
| $K_2HPO_4$ | 24–28 mM/L |

-continued

| | |
|---|---|
| $KH_2PO_4$ | 12–16 mM/L |
| Potassium citrate | 15–20 mM/L |
| L-carnitine, internal salt | 4–6 mM/L. |

*13. The method of claim 9, wherein said solution comprises 4–6 mM/L of said L-carnitine, said alkanoyl L-carnitine, or said pharmaceutically acceptable salt.*

*14. The transfusion bag of claim 10, wherein said preservative-anticoagulant solution is selected from ACD, CPD and CPDA-1.*

*15. The transfusion bag of claim 10, wherein said alkanoyl L-carnitine is selected from the group consisting of acetyl L-carnitine, propionyl L-carnitine, butyryl L-carnitine, isobutyryl L-carnitine, valeryl L-carnitine, and isovaleryl L-carnitine.*

* * * * *